(12) United States Patent
Halfmann et al.

(10) Patent No.: US 8,940,229 B2
(45) Date of Patent: Jan. 27, 2015

(54) DEVICE FOR IRRADIATING SURFACES

(75) Inventors: Helmut Halfmann, Rheinberg (DE);
Axel Hombach, Kuerten (DE); Markus Roth, Bonn (DE)

(73) Assignee: OSRAM AG, Munich (DE)

( * ) Notice: Subject to any disclaimer, the term of this patent is extended or adjusted under 35 U.S.C. 154(b) by 0 days.

(21) Appl. No.: 13/812,870

(22) PCT Filed: Oct. 26, 2011

(86) PCT No.: PCT/EP2011/068770
§ 371 (c)(1),
(2), (4) Date: Jan. 29, 2013

(87) PCT Pub. No.: WO2012/059383
PCT Pub. Date: May 10, 2012

(65) Prior Publication Data
US 2013/0216431 A1    Aug. 22, 2013

(30) Foreign Application Priority Data

Nov. 2, 2010   (DE) .......................... 10 2010 043 208

(51) Int. Cl.
| | | |
|---|---|---|
| A61L 2/00 | (2006.01) | |
| B01J 19/08 | (2006.01) | |
| H01T 19/04 | (2006.01) | |
| H05F 3/00 | (2006.01) | |
| A61L 2/10 | (2006.01) | |
| H01J 5/52 | (2006.01) | |
| H01J 61/30 | (2006.01) | |
| H01J 65/04 | (2006.01) | |

(52) U.S. Cl.
CPC ... *A61L 2/10* (2013.01); *H01J 5/52* (2013.01); *H01J 61/305* (2013.01); *H01J 65/046* (2013.01); *A61L 2202/11* (2013.01)

USPC .............. 422/22; 422/24; 422/121; 422/186; 422/186.3; 250/326; 250/492.1; 250/423 R; 204/157.15; 204/164

(58) Field of Classification Search
CPC ............... A61L 9/00; A61L 9/18; A61L 9/20; B05C 19/04; B05C 1/007
USPC .......... 422/22, 24, 121, 123, 186, 186.3, 306, 422/906–907; 250/326, 492.1, 423 R; 204/157.15, 164
See application file for complete search history.

(56) References Cited

U.S. PATENT DOCUMENTS

| | | |
|---|---|---|
| 4,837,484 A | 6/1989 | Eliasson et al. |
| 5,604,410 A | 2/1997 | Vollkommer et al. |

(Continued)

FOREIGN PATENT DOCUMENTS

| | | |
|---|---|---|
| DE | 3232537 A1 | 3/1984 |
| EP | 0254111 A1 | 1/1988 |

(Continued)

OTHER PUBLICATIONS

English language abstract for JP 2010125368 A dated Jun. 10, 2010.

(Continued)

*Primary Examiner* — Monzer R Chorbaji

(57) ABSTRACT

In various embodiments, a device for irradiating surfaces is provided. The device may include a radiation emitter having a radiation emitter vessel, wherein the radiation emitter vessel has at least one tunnel-like passage; and a structure configured to allow a process gas to flow through the at least one tunnel-like passage.

10 Claims, 2 Drawing Sheets

(56) References Cited

U.S. PATENT DOCUMENTS

| | | |
|---|---|---|
| 6,379,024 B1 * | 4/2002 | Kogure et al. .......... 362/263 |
| 6,624,428 B2 | 9/2003 | Hishinuma |
| 6,628,078 B2 | 9/2003 | Inayoshi |
| 6,657,392 B2 | 12/2003 | Hitzschke et al. |
| 6,734,444 B2 | 5/2004 | Fujitugu |
| 7,224,111 B2 | 5/2007 | Kling et al. |

FOREIGN PATENT DOCUMENTS

| | | |
|---|---|---|
| EP | 0607960 A1 | 7/1994 |
| EP | 1120121 A2 | 8/2001 |
| EP | 1232518 B1 | 11/2006 |
| EP | 1506567 B1 | 7/2007 |
| EP | 1873810 A1 | 1/2008 |
| JP | 2010125368 A | 6/2010 |
| WO | 2006056921 A2 | 6/2006 |
| WO | 2006087675 A2 | 8/2006 |

OTHER PUBLICATIONS

English language abstract of DE 3232537 A1 dated Mar. 1, 1984.

* cited by examiner

A-A

DEVICE FOR IRRADIATING SURFACES

RELATED APPLICATIONS

The present application is a national stage entry according to 35 U.S.C. §371 of PCT application No.: PCT/EP2011/068770 filed on Oct. 26, 2011, which claims priority from German application No.: 10 2010 043 208.3 filed on Nov. 2, 2010.

TECHNICAL FIELD

Various embodiments proceed on the basis of a radiation emitter or a device having a radiation emitter for irradiating surfaces by means of electromagnetic radiation. Various embodiments relate to a radiation emitter which emits shortwave ultraviolet (UV) radiation, e.g. below 200 nm. Radiation emitters of said type can be used inter alia for sterilizing level or curved surfaces, for example.films, as well as the interior of bottles, canisters or other hollow containers.

BACKGROUND

In the UV irradiation of surfaces, in particular for sterilization purposes, it can be advantageous if at least during the irradiation, where appropriate also before and/or after, a purging of the spatial area between radiation emitter and surface takes place using a purging gas. This is intended to remove UV-radiation-absorbing gases between the surface and the UV radiation emitter, at least during the irradiation. Nitrogen or noble gases in particular are suitable as a purging gas. In other irradiation processes, too, a defined atmosphere between radiation emitter and surface, and consequently the use of a suitable process gas, may be advantageous. The term process gas is used in the following as a generic term for one or more suitable gases for purging or for other processes before, during and/or after the irradiation.

In order to irradiate readily accessible surfaces, for example flat films, the prior art approach has been to supply the purging gas by means of a separate device arranged around the radiation emitter or from the side. A disadvantageous aspect is the requirement for additional equipment and the necessary coordination between purging arrangement and radiation emitter. Furthermore, said systems generally cannot be used inside hollow spaces with narrow access openings such as canisters or bottles for space reasons.

A UV radiation emitter based on a one-sided dielectric barrier discharge is known from the publication EP 1 506 567 B1. For this purpose the discharge vessel 2 is filled with xenon. So-called excimers are formed during the gas discharge, which preferably is driven by means of a pulsed operating method described in U.S. Pat. No. 5,604,410. Excimers are excited molecules, e.g. Xe2*, which emit electromagnetic radiation when returning to the usually unbound ground state. In the case of Xe2*, the maximum of the molecule band radiation lies in the region of approx. 172 nm. In order to generate the dielectric barrier discharge, a first helix-shaped electrode 23 is arranged coaxially inside the tubular discharge vessel 2. Six strip-shaped outer electrodes 8a-8f are arranged in parallel with one another and mutually spaced apart on the outside of the discharge vessel 2.

A tubular UV radiation emitter based on a two-sided dielectric barrier discharge is disclosed in the publication EP 0 607 960 A1. The radiation emitter vessel is formed in the manner of a coaxial double tube arrangement in which an inner tube and an outer tube are joined to one another to form a gas-tight seal at the two front ends. In this arrangement the discharge chamber enclosed by the discharge vessel extends between inner and outer tube.

A flat discharge lamp based on a two-sided dielectric barrier discharge is disclosed in the publication EP 1 232 518 B1. The dielectric barrier discharge is generated between a base plate and a top plate, the circumferential sealing frame and cone-shaped supporting elements being molded into the top plate. The electrodes are applied as two interlocking comb-like line structures onto the outside of the base plate.

SUMMARY

Various embodiments may provide a device which enables surfaces to be irradiated under a defined atmosphere and at the same time may avoid the described disadvantages of the prior art.

Various embodiments provide a device for irradiating surfaces having a radiation emitter which includes a radiation emitter vessel, the radiation emitter vessel having at least one tunnel-like passage, and a means which is designed to allow a process gas to flow through the at least one tunnel-like passage.

Particularly advantageous embodiments can be found in the dependent claims.

Protection is also claimed for the use of the inventive device for sterilizing level or curved surfaces.

The basic concept of the invention consists in carrying out the gas purging by means of a process gas, for example an inert gas such as nitrogen or a noble gas, not with the aid of a separate device, but in suitably developing a radiation emitter in such a way that a purging gas can emerge from the radiation emitter.

For this purpose the device according to the invention includes a radiation emitter which is embodied in such a way that the process/purging gas can exit from the radiation emitter vessel itself and thereby be supplied to the spatial area between radiation emitter and surface requiring to be irradiated. The radiation emitter can additionally have a radiation emitter base which is likewise embodied in such a way that the purging gas can also flow out from the radiation emitter base. This reduces not just the amount of equipment required but also the time needed, in particular for the irradiation of the internal surfaces of hollow bodies, where previously a gas exchange prior to the irradiation was usually necessary. The amount of space required for the device is also reduced.

For this purpose the radiation emitter vessel has at least one tunnel-like passage which is connected to a means which is designed to allow a process gas to flow through the tunnel-like passage. In the simplest case a gas line or similar is introduced for this purpose into the entrance of the tunnel-like passage or connected to the entrance in some other way. Alternatively the gas supply can be provided by way of a radiation emitter base which is connected to a gas line, for example by a gas hose being attached to a gas nipple at the end of the base. Internally the radiation emitter base is configured in such a way that the process gas flows out of the gas line into the entrance of the tunnel-like passage. In this case it can also be provided that a switchover can be made—at least temporarily—from gas supply to gas removal.

By way of precaution let it be made clear that the process gas obviously does not pass through, enter or exit the discharge space itself. Rather, the discharge space, in which a gas discharge generates the radiation during operation, is also hermetically sealed in the region of the passages by means of their tunnel-like embodiment. As a result the process gas can flow through the tunnel-like passages without affecting the gas discharge generated inside the hermetically sealed discharge vessel.

In addition the radiation emitter base can have one or more gas orifices which are likewise connected to the gas means. Where appropriate the at least one gas orifice of the radiation emitter base is preferably oriented such that the gas can flow in the direction of the radiation emitter vessel or into the neighboring space region with the surface requiring to be irradiated. For the sterilization of hollow containers such as bottles or canisters, the device having the radiation emitter and in particular the radiation emitter vessel itself are embodied as elongate in order to be able to be introduced through the opening of the container. A base, shaped like a cup for example, can be arranged at one end of the elongate radiation emitter vessel.

Particularly suitable for these purposes is a radiation emitter having a radiation emitter vessel having an inner tube and an outer tube which are connected to one another to form a gastight seal in the manner of a coaxial double tube arrangement. Since in this arrangement the discharge space enclosed by the discharge vessel extends between inner and outer tube, the interior of the inner tube can be used as a tunnel-like passage through which the purging gas can flow. For this purpose the purging gas is supplied at one end of the inner tube and exits again at its other end. As a result the purging gas emerges at the front end of the radiation emitter vessel and consequently in immediate proximity to the radiation exiting at the front end or, more specifically, to the surface requiring to be irradiated in this area.

It can furthermore be advantageous if the radiation emitter base additionally has at least one gas orifice which is preferably oriented in the direction of the radiation emitter vessel. This enables the purging gas to flow along the length of the radiation emitter vessel and purge the neighboring spatial region of the surface that is to be irradiated. A particularly efficient surface treatment, in particular sterilization, is possible as a result of this close coupling, both spatially and in terms of equipment, of purging gas flow and irradiation.

In order to supply the purging gas, the radiation emitter can be provided with a connecting terminal to which a gas line can be attached. The purging gas supplied centrally by way of a connected gas line can be conveyed to the inner tube and where applicable one or more gas orifices in the radiation emitter base by way of a gas distribution chamber provided for example in the radiation emitter base. Alternatively the gas line can also project into the inner tube or be routed at least as far as the input-side end of the inner tube. This alternative is suitable primarily when no gas orifices are provided in the radiation emitter base or no base at all is provided for the radiation emitter. Furthermore, a gas evacuation hose can also be provided in addition in the inner tube.

In addition, one or more gas orifices or tunnel-like passages can also be provided generally for evacuating the gas. This is advantageous in particular for the sterilization of hollow containers such as bottles or canisters with narrow container openings, where possibly there is little space remaining for the process gas to flow away. In an embodiment of the device according to the invention a seal is also provided between radiation emitter and container opening in order to prevent ambient air permeating into the container. In this case the process gas flows away solely via the gas orifices provided for this purpose in the radiation emitter. As well as serving for the irradiation of hollow containers, the inventive device having an elongate radiation emitter is generally also suitable for irradiating extensive, for example curved or plane, surfaces. For the latter, however, an alternative embodiment variant is also particularly suitable in which the radiation emitter and in particular the radiation emitter vessel have a flat shape. In other words this alternative is based on a so-called flat lamp which has possibly been modified for the type of radiation desired, in particular UV radiation for sterilization purposes. The flat radiation emitter vessel likewise has at least one tunnel-like passage which is formed between its radiation-emitting front side and the opposite rear side. Optionally, the base, in this case in the shape of a frame for example, additionally has at least one gas orifice from which the supplied process gas can emerge. For further details the reader is referred to the exemplary embodiments shown in the figures.

In general the radiation emitter vessel consists at least in sections of a material that is transparent to the radiation, preferably quartz glass in the case of UV radiation.

For the purpose of generating UV radiation the radiation emitter is preferably designed to induce a dielectric barrier discharge in the interior of the radiation emitter vessel. For further details on this subject the reader is referred to the publications EP 1 506 567 B1, U.S. Pat. No. 5,604,410 and EP 1 232 518 B1 cited in the introduction.

BRIEF DESCRIPTION OF THE DRAWINGS

The invention shall be explained in more detail below with reference to exemplary embodiments taken in conjunction with the accompanying figures, in which:

FIG. 2b shows a longitudinal sectional view of the device from FIG. 2a.

DETAILED DESCRIPTION

The following detailed description refers to the accompanying drawings that show, by way of illustration, specific details and embodiments in which the invention may be practiced.

Figure 1A:
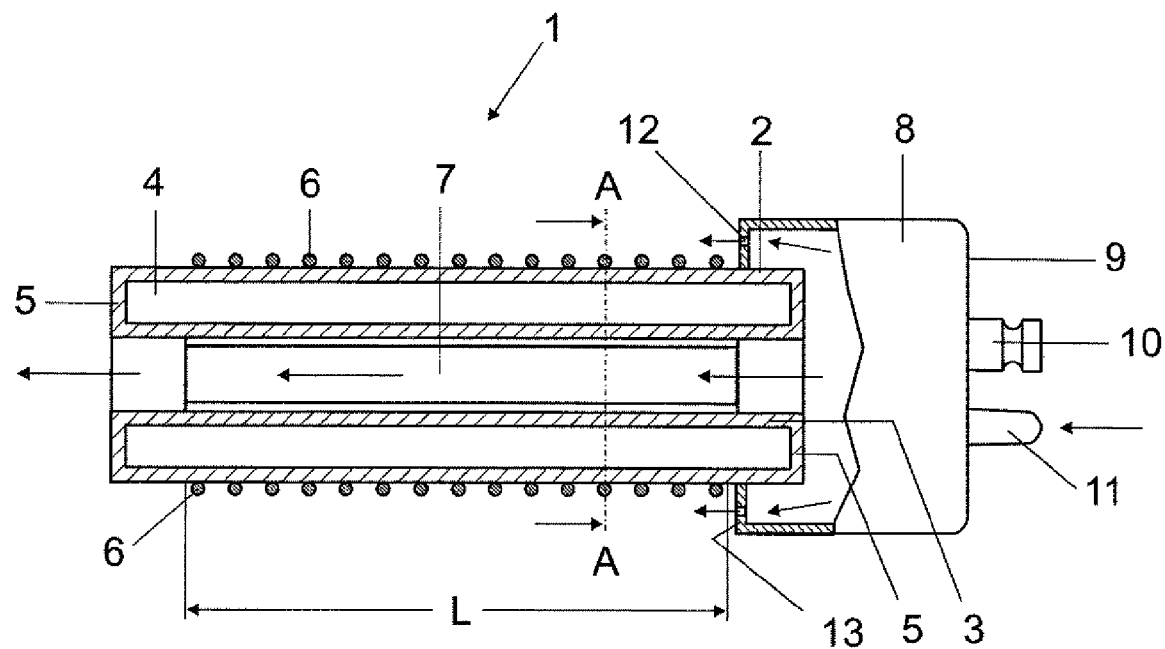
FIG. 1a shows a partial longitudinal sectional view of an inventive device having a tubular radiation emitter.
Figure 1B:
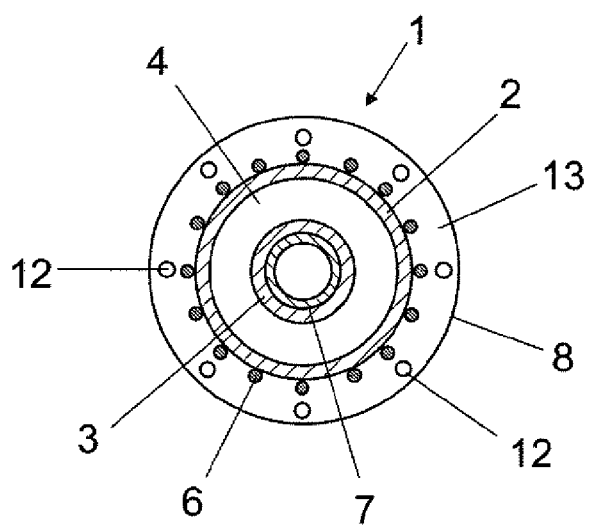
FIG. 1b shows a cross-sectional view of the device from FIG. 1a, FIG. 2a shows a plan view onto an inventive device having a flat radiation emitter.

FIGS. 1a, 1b show in an extremely schematic representation a partially sectioned longitudinal view and a cross-sectional view of a first exemplary embodiment of the inventive device 1 having a tubular radiation emitter based on a dielectric barrier discharge. Said device is provided in particular for the sterilization of hollow containers, for example bottles and canisters. The elongate discharge vessel of the radiation emitter consists of an outer tube 2 and an inner tube 3 in a coaxial double tube arrangement which thus define the longitudinal axis of the discharge vessel. The length of the tubes 2, 3 varies according to application. For sterilizing bottles, for example, the length is preferably dimensioned such that the internal surface of the bottle is irradiated completely when the radiation emitter is inserted. The diameters of the tubes are likewise preferably adjusted according to the application. In particular the largest external diameter of the discharge vessel is dimensioned such that the device 1 can be introduced together with the radiation emitter into the container provided for the irradiation, for example through the bottle neck into a bottle. Both tubes 2, 3 consist of quartz glass which is permeable to UV radiation. Furthermore, the discharge vessel is sealed at its two front ends in such a way that an elongate, annular-gap-shaped discharge space 4 is formed. For this purpose the discharge vessel has suitably shaped, ring-like vessel sections 5 in each case at its two ends. Also attached to one of the vessel sections 5 is an exhaust tube (not shown) with the aid of which the discharge space 4 is first evacuated and then filled with 15 kPa xenon. A wire gauze 6 which forms the outer electrode of the radiation emitter is fitted on the outside of the wall of the outer tube 2. Alternatively, a narrow, spiral-shaped metal track for example can also be applied for this purpose. Arranged in the interior of the inner tube 3, i.e. likewise outside of the discharge space 4 enclosed by the discharge vessel, is a metal tube 7 which forms the inner electrode of the lamp. Alternatively, a conductive layer, e.g. made of carbon, can also be used for this purpose for example. A cup-shaped base 8 is arranged at one end of the discharge vessel. The front end 9 facing away from the discharge vessel has an electrical connector 10 for connecting the supply voltage for the radiation emitter 1. Also mounted on the front end 9 is a gas connection nipple 11 to which a purging gas hose can be attached. The purging gas flowing in via the gas connection nipple 11 passes through the interior of the base 8 to the base-side end of the inner tube 3, thus being able to flow into the latter and flow out at its other end. In addition to its function as a component of the discharge vessel, the inner tube 3 therefore also serves as a tunnel-like passage for the purging gas flow. Furthermore, the purging gas can flow out of a total of eight gas orifices 12 which are arranged uniformly distributed around the circumference in the ring-shaped base projection 13 from which the discharge vessel protrudes.

Figure 2A:
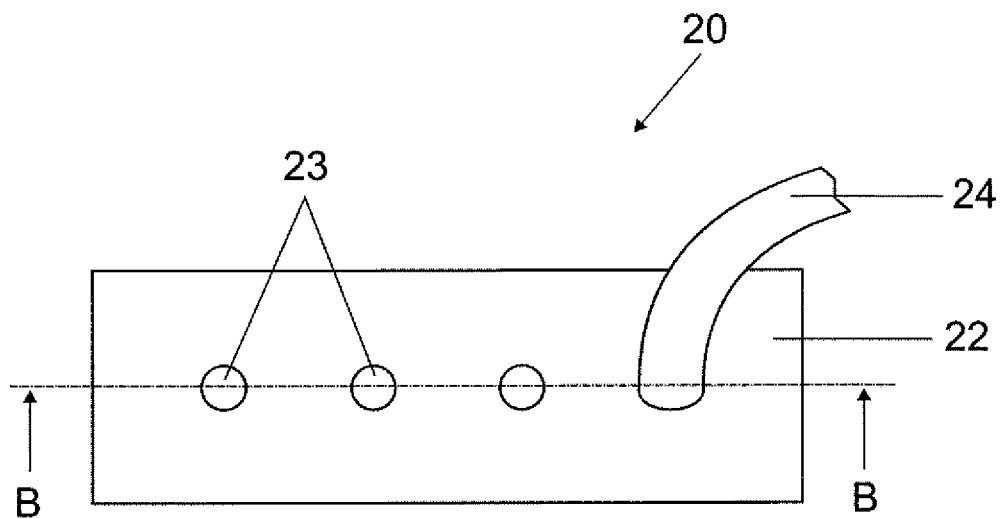
Figure 2B:
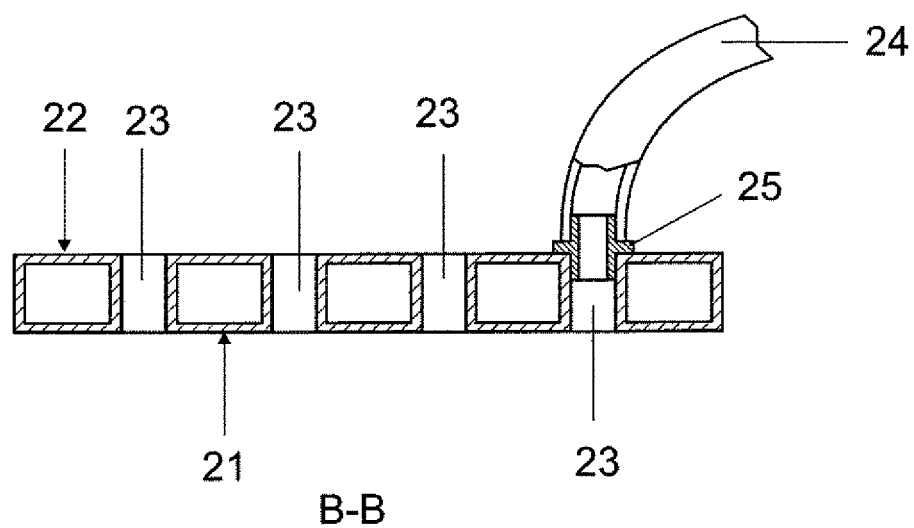

FIGS. 2a, 2b show in an extremely schematic representation a plan view and a partial longitudinal section of an inventive device 20 having a flat radiation emitter. Depicted here is a modified flat lamp based on a dielectric barrier discharge such as is known for example from the publication EP 1 232 518 B1 cited in the introduction. The otherwise customary luminescent substance is dispensed with for the sterilization by means of UV radiation. Furthermore, the flat discharge vessel is made of quartz glass on account of the requisite transparency to UV radiation. The discharge vessel itself has a rectangular basic shape with a UV-radiation-emitting front side 21 and an opposite rear side 22. Embodied between front and rear side are four tunnel-like passages 23 which are arranged next to one another centrally with respect to the transverse side and in the direction of the longitudinal side. In the case of a flat lamp of the type disclosed in the initially cited EP 1 232 518 B1, for example, the tunnel-like passages can be created by driving through in a gas-tight manner one or more of the cone-like supporting elements formed from the flat vessel parts. In this case the tunnel-like passage is not necessarily required to have a constant diameter as shown in FIGS. 2a, 2b. Rather, it can also be advantageous if the passage narrows conically in the direction of the front side in the manner of a flow nozzle, provided in any event that a sufficiently large aperture still remains for the gas to flow. The passage on the right in FIGS. 2a, 2b is provided with a purging gas hose 24 which is connected with the aid of a hose connecting piece 25 inserted into the passage from the rear side 23. This causes the process gas to flow out from the exit of the passage essentially vertically with respect to the emission surface. The remaining three passages can be used to remove the process gas or some of them, or even all three, can likewise be provided with a purging gas hose for supplying additional purging gas. In addition, the flat radiation emitter can also be provided with a base (not shown) arranged at least on a narrow side or else also extending circumferentially in a frame shape. The base preferably projects beyond the front side of the flat radiation emitter vessel and has a plurality of gas orifices which are arranged in such a way that the purging gas can flow laterally over the front side of the flat radiation emitter and consequently also over the immediately adjacent surface that is to be irradiated during the irradiation.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A device for irradiating surfaces, comprising: a radiation emitter comprising a radiation emitter vessel, wherein the radiation emitter vessel has at least one tunnel-like passage; and a structure configured to allow a process gas to flow through the at least one tunnel-like passage,
wherein the radiation emitter vessel comprises an inner tube and an outer tube which are connected to one another to form a gas-tight seal in the manner of a coaxial double tube arrangement; and wherein the inner tube cooperatively interacts with the structure for the process gas, as a result of which the inner tube serves as a tunnel-like passage for the gas flow of the process gas and the process gas emerges at the front end of the radiation emitter vessel.

2. The device as claimed in claim 1, wherein the structure which is designed to allow a process gas to flow through the at least one tunnel-like passage comprises a supply line for the process gas which is connected to the entrance of the at least one tunnel-like passage.

3. The device as claimed in claim 1, further comprising: a base which is arranged on the radiation emitter vessel.

4. The device as claimed in claim 1, wherein the base has at least one gas orifice.

5. The device as claimed in claim 1, wherein the structure which is designed to allow a process gas to flow through the at least one tunnel-like passage comprises at least one connecting terminal for supplying the process gas, the at least one connecting terminal being connected to the at least one tunnel-like passage.

6. The device as claimed in claim 5, wherein the base has at least one gas orifice; wherein the at least one gas connecting terminal is additionally connected to the at least one gas orifice in the base.

7. The device as claimed in claim 1, wherein the radiation emitter vessel consists at least in sections of a material which is transparent to the radiation.

8. The device as claimed in claim 1, wherein the radiation emitter is designed for the emission of UV radiation.

9. The device as claimed in claim 1, wherein the radiation emitter is designed to induce a dielectric barrier discharge in the interior of the radiation emitter vessel.

10. A method for the sterilization of a surface, the method comprising: providing a device for irradiating surfaces, the device comprising: a radiation emitter comprising a radiation emitter vessel, wherein the radiation emitter vessel has at least one tunnel-like passage; and a structure configured to allow a process gas to flow through the at least one tunnel-like passage; sterilizing the surface using the device,
wherein the radiation emitter vessel comprises an inner tube and an outer tube which are connected to one another to form a gas-tight seal in the manner of a coaxial double tube arrangement; and wherein the inner tube cooperatively interacts with the structure for the process gas, as a result of which the inner tube serves as a tunnel-like passage for the gas flow of the process gas and the process gas emerges at the front end of the radiation emitter vessel.

* * * * *